United States Patent [19]

Gago et al.

[11] Patent Number: 5,044,116

[45] Date of Patent: Sep. 3, 1991

[54] COATED SEEDS AND A PROCESS FOR THEIR OBTAINMENT

[75] Inventors: Ignace Gago, Braine-l'Alleud; René Detroz, Ohain, both of, Belgium

[73] Assignee: Interox (Société Anonyme), Brussels, Belgium

[21] Appl. No.: 679,351

[22] Filed: Dec. 7, 1984

[30] Foreign Application Priority Data

Dec. 12, 1985 [FR] France ............................... 83 19981

[51] Int. Cl.$^5$ ................................................ A01C 1/06
[52] U.S. Cl. .......................................... 47/57.6; 427/4
[58] Field of Search .................. 47/56, DIG. 9, 57.6, 47/74; 427/4

[56] References Cited

U.S. PATENT DOCUMENTS

| | | | |
|---|---|---|---|
| 1,486,431 | 3/1924 | Harvey | 47/57.6 |
| 2,083,065 | 6/1937 | Heyl | 47/DIG. 9 |
| 3,698,133 | 10/1972 | Schreiber | 47/57.6 |
| 3,812,619 | 5/1974 | Wood et al. | 47/58 |
| 3,867,324 | 2/1975 | Clendinning et al. | 47/74 |
| 3,908,308 | 9/1975 | Meyers | 47/56 |
| 3,920,436 | 11/1975 | Janssen | 47/57.6 |
| 3,991,517 | 11/1976 | Lewis | 47/57.6 |
| 4,149,869 | 4/1979 | Lloyd | 47/57.6 |
| 4,251,952 | 2/1981 | Porter et al. | 47/57.6 |
| 4,339,456 | 7/1982 | Rushing | 47/DIG. 9 |
| 4,344,979 | 8/1982 | Gago et al. | 47/4 |
| 4,383,391 | 5/1983 | Thomas | 47/57.6 |
| 4,399,633 | 8/1983 | Haughey et al. | 47/57.6 |
| 4,495,724 | 1/1985 | Kirkland et al. | 47/57.6 |

FOREIGN PATENT DOCUMENTS

| | | | |
|---|---|---|---|
| 69711 | 6/1977 | Japan | 47/57.6 |
| 1294161 | 10/1972 | United Kingdom | 47/57.6 |
| 1399822 | 7/1975 | United Kingdom | 47/56 |
| 1580248 | 11/1980 | United Kingdom | 47/57.6 |

OTHER PUBLICATIONS

Collins, E. P., "Seed Coatings", *Garden*, Mar./Apr. 1981, pp. 14, 16, 17 and 29.

*Primary Examiner*—James R. Feyrer
*Attorney, Agent, or Firm*—Spencer & Frank

[57] ABSTRACT

The seeds are coated with a polyester with a low melting point and a peroxy compound.

The process involves treating the seeds with a peroxy compound in the presence of a solution of the polyester in an organic solvent or with the polyester in the liquid or melted state.

16 Claims, No Drawings

COATED SEEDS AND A PROCESS FOR THEIR OBTAINMENT

The present invention relates to coated seeds and a process for obtaining coated seeds.

The coating of seeds has become a common practice. Its purpose in particular is to improve the characteristics of germination, to provide various additives capable of playing a part at any time during the establishment and growth of plants, to protect the seeds or to give the seed a shape or size that are suitable for automatic sowing. It has thus been proposed to coat seeds with nutrients, fillers, fungicides, herbicides, insecticides etc.

It has also been proposed to incorporate calcium peroxide in the coating agent in order to improve the germinating capacity of beet seeds (Belgian patent 859 566 filed on Oct. 11, 1977 in the name of the applicant).

The known coating processes, however, have many disadvantages.

It is a frequent occurrence that the coating agent does not adhere properly to the seed with the result that it is not resistant to the various handling procedures which seeds undergo. This phenomenon is particularly noticeable with seeds that absorb water rapidly. Indeed, during the coating operation, substantial swelling of certain seeds due to the absorption of water is frequently observed. After drying, the seed contracts and resumes its original size, whereas the coating agent does not generally contract in the same proportions; as a result, it no longer adheres properly to the seed and becomes brittle, splits or disintegrates.

Certain coating agents, on the other hand, are so hard and resistant that they do not dissolve nor do they disintegrate easily under the effects of moisture and water once the seed is in position, which characteristic is equally detrimental During the coating operation, small quantities of water are used in particular to moisten the seeds before the coating operation proper, to solubilise or disperse at least one of the coating constituents or to solubilise or disperse the binders used to ensure the adhesion of the other coating constituents. The presence of water has some disadvantages which are particularly significant if the seeds are poorly protected and absorb water rapidly. Indeed, certain seeds are able to absorb water during the coating operation which may lead to the premature onset of germination with the result that the seeds can no longer be stored. Moreover, it is often not possible to dry the seed correctly beneath the layer of coating agent which leads to risks of degradation during storage. These effects are particularly noticeable if the seeds used are seeds of leguminous plants, maize and cruciferae.

Moreover, certain constituents of the coating agent which on the whole have advantageous properties, may have secondary phytotoxic effects on certain seeds.

Indeed, in some cases, it is difficult to coat seeds in a uniform manner because their surfaces are not very even and do not permit uniform adhesion of the coating agents. The binders that are normally used to make the other constituents of the coating agent adhere to the seed do not enable all these disadvantages to be overcome simultaneously.

The purpose of the present invention is to procure coated seeds and a process for their obtainment which do not have the respective disadvantages of the known seeds and the known processes.

In the coated seeds according to the invention, the coating agent is highly resistant particularly to embrittlement and splitting under dry conditions and it adheres well to the seeds with the result that the stability of the coated seeds during storage is excellent. The coating agent splits, disintegrates or dissolves under the effects of humidity or water when the seeds are sown in their culture medium. Moreover, it does not have any phytotoxic effect and it is able to prevent premature germination of the seeds.

The coated seeds according to the invention have an excellent rate of germination and a substantial reduction in the time required for the seeds to sprout is observed. If the coating agent contains active additives, these are liberated slowly, which enables their activity to be maintained over a fairly long period. Moreover, the invention procures seeds that may contain plant health products making it possible to avoid undertaking certain manipulations at the time of sowing which often have a certain degree of toxicity for the users.

The process according to the invention has the advantage of not requiring the use of water during the seed coating operation and thus of avoiding all the disadvantages associated with its use.

To this end, the present invention relates to seeds coated with a coating agent containing a peroxy compound according to which the coating agent is anhydrous and also contains a polyester.

The term polyesters with a low melting point is intended to mean those whose melting point does not exceed 80° C. and preferably 60° C. Generally, the polyesters are chosen from those whose melting point is below 60° C.

Various types of polyesters are suitable. Polyesters with a low melting point are generally suitable, especially those with a melting temperature not exceeding 80° C., and preferably 60° C. The polyesters can be homopolymers or copolymers. Generally, the polyesters are chosen from the homopolymers and copolymers of lactones such as ε-caprolactone and δ-valerolactone. Most often, they are chosen from the homopolymers and copolymers of ε-caprolactone.

The copolymers of lactones can contain various types of comonomeric units. Generally, they are copolymers of a lactone with an olefine oxide such as ethylene oxide or propylene oxide, with a lactam such as caprolactam with another lactone; or with a mixture of a glycol such as ethylene glycol or a dicarboxylic acid, preferably aliphatic, such as adipic acid. The copolymers of lactones can contain variable quantities of monomeric units derived from the lactone. Generally, they contain at least 10% and most often at least 20% of their weight of monomeric units derived from the lactone. Most often, this proportion does not exceed 95% and preferably 90% of the weight of the polymer.

Polyesters of the homopolymer type are highly suitable. Of these, homopolymers of lactones are particularly suitable. Homopolymers of ε-caprolactone have given excellent results.

The polyesters according to the invention can have variable average molecular weights. Generally, their average molecular weight is at least 300 and most often at least 500. Generally, their average molecular weight does not exceed 60,000 and most often 50,000. Excellent results have been obtained with polyesters with an average molecular weight of about 800 to about 10,000.

All the types of organic or inorganic peroxy compounds can be used in the seed coating agent according to the invention. Mixtures of peroxy compounds are also suitable. The organic peroxy compounds that can be used include compounds such as benzoyl peroxide and its halogenated derivatives, alkyl perbenzoates such as tert.butyl perbenzoate, p-menthane hydroperoxide and the addition products of hydrogen peroxide such as urea peroxide. The inorganic peroxy compounds are generally chosen from persalts such as the perborates, percarbonates, persulphates, perphosphates of alkali metals or alkaline earth metals and metal peroxides. Most often it is preferable to use inorganic peroxy compounds such as metal peroxides, more particularly alkaline earth metal peroxides. Very good results have been obtained by using calcium peroxide or magnesium peroxide. The best results were obtained with calcium peroxide. If the compound is calcium peroxide, a commercial product containing 30-90% by weight calcium peroxide is generally used, the remainder being composed mainly of calcium hydroxide and possibly of a salt of calcium and water. Other grades of calcium peroxide may also be suitable.

The coating agent can also contain various additives. It can thus contain organic or mineral-type fillers. It is also possible to incorporate mixtures of fillers. The fillers are fine powders generally having a granulometry such that they pass through a screen of 170 and preferably 325 mesh (US standard). Natural products based on cellulose such as the powder derived from wood or peat flour are generally used as organic-type fillers. Products based on silica, silicates, carbonates, calcium salts are used as inorganic-type fillers. Fillers chosen from crushed or precipitated silica, crushed sand, bentonite, talcum, kaolin, diatomaceous earths, fuller's earths, vermiculite, clay, limestone, chalk, calcium carbonate, calcium oxide, calcium hydroxide, gypsum and mixtures thereof are generally used. Non-phytotoxic fillers are generally used.

The coating agent can also contain one or more other additives such as plant health products, more particularly insecticides, nematicides, fungicides, disinfectants, repellants, herbicides and growth regulators, agents capable of protecting seeds from the harmful effects of selective herbicides such as activated carbon, nutrients (fertilisers), agents capable of improving the germination and quality of the products, bacteria capable of exerting a favourable effect on the germination, establishment or growth of plants etc.

Good results are obtained when the coating agent contains a nutrient.

Good results are obtained when the coating agent contains plant health products and more particularly fungicides. Examples of suitable fungicides are given in the Liste des Produits Phytopharmaceutiques (List of phytopharmaceutical products) published by the Ministère de l'Agriculture, Service de la Protection des Végétaux, Brussels, 1968 and 1981 and in the Index Phtyosanitaire (health product index) published by the ACTA, Paris, 1981, pages 195 to 268. Methoxyethyl mercury acetate, benomyl, captan, copper oxyquinoleate, thiram, thiabendazole, ethyrimol, maneb, and captafol are highly suitable. Good results have been obtained with benomyl, captan and methoxyethyl mercury acetate.

The total amount of coating agent can vary widely depending on the type of seeds, their shape and size. The total amount of coating agent is generally at least 0.0001 times the weight of the seeds. Most often, this quantity does not exceed 100 times the weight of the seeds but this limit is not critical. If it is not necessary to give the coated seeds a pre-determined shape or size, the quantity of coating agent is most often at least 0.01 and preferably at least 0.1% of the weight of the seeds and it does not generally exceed 300% and preferably 200% of their weight. If it is desired that the seeds be given a pre-determined shape and size, the quantity of coating agent is generally at least 0.5 and most often at least one times the weight of the seeds and it does not generally exceed 100 and most often 50 times their weight.

The quantities of polyesters in the coating agent according to the invention can vary widely. They can be from 0.01 to 90% of the total weight of the coating agent. Generally, the polyester content represents 1 to 60% of the weight of the coating agent, excluding the fillers.

The quantity of peroxy compound present in the coating agent can vary widely. It is generally between 0.1 and 99% of the total weight of the coating agent. Most often, the coating agent contains 1 to 90% by weight of peroxy compound. Good results have been obtained when the peroxy compound content represents 10 to 80% of the weight of the coating agent, excluding the fillers.

The filler content can vary very widely. It is generally between 0 and 99% of the total weight of the coating agent and preferably between 0.1 and 99% of the total weight of the coating agent. Contents between 1 and 98% are highly suitable.

The other additives can be present in variable proportions up to 95% of the weight of the coating agent. The content of these other additives is generally 0.00001 to 95% of the weight of the coating agent. Generally, the content of these other additives represents 0.1 to 95%, and most often 5 to 90% of the weight of the coating agent, excluding the fillers.

Particularly advantageous coating agents can thus contain 5 to 60% by weight of polyesters according to the invention, and 40 to 95% by weight of peroxy compounds, the coating agent being present in quantities of 0.01 to 200% of the weight of the uncoated seeds. These coating agents can also contain up to 20% and most often 0.1 to 20% of their weight of various additives.

Other equally advantageous coating agents can contain 0.1 to 50% by weight of polyesters according to the invention, 30 to 75% by weight of peroxy compounds and 20 to 60% by weight of various additives, the coating agent being present in quantities of 0.01 to 300% of the weight of the uncoated seeds.

Other particularly advatangeous coating agents can contain 0.1 to 20% by weight of polyesters according to the invention, 0.1 to 30% by weight of peroxy compounds, 30 to 99.7% by weight of fillers and 0.01 to 30% by weight of other additives, the coating agent being present in quantities of 0.5 to 100 times the weight of the uncoated seeds. The latter are suitable if the seeds are to be given a pre-determined shape or size.

The invention can be applied to various types of seeds such as the seeds of leguminous plants, graminaceous plants, or dicotyledonous plants. Generally, it is used for the seeds of leguminous plants such as the various sorts of peas, beans and lentils, lucerne, clover, vetch, soya, ground nuts, field beans and lupin, the seeds of graminaceous plants such as ray grass and cereals (maize, oats, rye, wheat, millet, sorghum, barley, rice etc), the seeds of dicotyledonous plants such as chicory, lettuce, tobacco, tomato, carrot, cabbage and colza and the seeds of cruciferae such as radishes. Good results are obtained with seeds of leguminous plants such as the seeds of peas and soya and with the seeds of graminaceous plants such as barley, oats and six-row barley.

The present invention also relates to a process for coating seeds. According to the invention, seeds are mixed with the peroxy compound, a layer of liquid or molten polyester is applied on them and the polyester is solidified onto the seeds. The application of the polyester layer may be realised by various techniques such as dipping of the seeds in a bath containing the polyester or spraying of the polyester on the seeds. The spraying application technique is preferred.

According to a particular embodiment of the invention, the seeds are given a rotating motion, they are mixed with the peroxy compound and coated with the polyester.

Any process and more particularly any coating device able to give the seeds a rotating motion such a belt conveyors, containers of various shapes, spherical or cylindrical open devices, devices used for the mixing of liquids or solids, granulators, rotating drums, revolving plates are suitable to carry out the process according to the invention.

Generally, devices with rounded or spherical edges which can be tilted on their axle.

Preferably a rounded edges container is used which is given a planetary motion and which rotation axle may be tilted from 0° to 90° with respect to the vertical.

Generally, polyesters contained in the coating are chosen amongst those which melting temperature is below 80° C., preferably 60° C.

Coating can be carried out accordng to various methods. The polyester can be used as such in the liquid or melted state or in the form of a solution in an organic solvent.

A particular method involves treating the seeds with the peroxy compound and with the polyester in the liquid or melted state. According to this particular method, the polyester is selected amongst those which melting temperature is below 80° C., preferably 60° C. It is thus possible to apply the polyester to the seeds and to add the peroxy compound simultaneously, consecutively or alternately. If necessary, it is also possible to add fillers or any other additives at any time during the coating operation. Generally, the polyester is applied to the seeds in the liquid or melted state and the peroxy compound and the fillers or any other additives are added afterwards. The introduction of the polyester in the liquid or melted state can take place whilst the peroxy compound and the fillers or any other additives are being introduced. It is possible to interrupt the introduction of the peroxy compound and the fillers or any other additives once or more and to undertake a fresh application of polyesters in the liquid or melted state in the meantime until the seeds are completely coated. According to this particular technique, the seeds coating device has to be preheated at a temperature laying between 45° and 80° C. so as to maintain the polyester at its softening point. The polyester is sprayed onto the seeds rotating in the coating device by any appliance able to divide it in small droplets, for example by a pneumatic spray-gun.

In the process according to the invention the polyester is risen in the tank of the spray-gun appliance at a sufficient high temperature for maintaining it in the molten state. The coating device temperature and the temperature of the spray-gun appliance are not critical and are subject to the nature of the polyester. They have nevertheless to be carefully determined in each particular case for the polyester used and are straight related to the softening and melting temperatures of said polyester. Generally, the temperature of the spraying appliance is adjusted within a range from 10° to 40° C. above the softening temperature of the used polyester and preferably, from 20° to 30° C. above this temperature. The coating device temperature is the most often adjusted within the range from 0,5 to 10° C. above the softening temperature of the used polyester and, preferably, from 1° to 5° C. above this temperature.

Another method involves using the polyester in the form of a solution in an organic solvent. The sequence of operations is similar to those used for coating with polyesters in the liquid or melted state.

Various organic solvents can be used to this end. They are generally chosen from organic solvents having aromatic groups or organic solvents substituted by halogens such as chlorine and bromine. nitro groups, carbonyl groups, carboxyl groups, ester groups and alkoxy groups. It is also possible to use mixtures of solvents. It is thus possible to use mixtures of the abovementioned solvents or of said solvents with alcohols. The solvents are most often chosen from organic compounds containing 1-12 carbon atoms; if said compounds are aromatic compounds their number of carbon atoms is 4-12. The alcohols generally contain 1-8 carbon atoms.

Good results have been obtained with halogenated solvents or more particularly chlorinated solvents alone or in mixture with alcohols.

The best results have been obtained with a chloromethane such as methylene chloride alone or in mixture with an alcohol such as methanol.

The solutions of polyesters can contain variable quantities of polyesters. Generally, for reasons of economy, solutions whose concentration is equal to or close to saturation are used. Good results are obtained with solutions containg 10 to 60% of their weight of polyesters.

After coating, seeds are spread out in a small width layer onto a flat surface. If the polyester is used in the form of a solution, the seeds are moreover dried after coating in order to blow out the residual solvent of the coating. Coating can take place according to any method known in itself such as by passing a current of forced air, possibly heated, over the seeds which can be placed to this end in equipment such as sieves, or by drying by natural ventilation.

In order to illustrate the invention yet without limiting its scope, some practical examples of implementation are given below.

EXAMPLE 1R to 2

COATING AND GERMINATION OF SOYA SEEDS 200 g of soya seeds of the Corsoy variety were inserted in a circular drum of 40 cm of diameter with rounded edges and actuated with a rotating motion of 50 rotations/min. The tilting of the rotating axle of the drum was then adjusted so as to give it an angle of 60° with the vertical.

With a pneumatic spray-gun of the type air-brush equiped with a needle spraying head of 3 mm of diameter, a total of 0.28 g of a solution containing 50 weight % of poly-ε-caprolactone and 50% of methylene chloride ($CH_2Cl_2$) was sprayed in 3 successive steps.

As soon as the seeds were slightly and regularly coated by the polycaprolactone 20 g of commercial powder of calcium peroxyde of 60 weight % of $CaO_2$ and of mean diameter of 8 μm were progressively inserted by means of a vibrating dosing appliance which nose has its extremity inside the drum. When the flow of powder was continuously and regularly established, an additional quantity of 2.52 g of the polycaprolactone solution in the $CH_2Cl_2$ was sprayed at the same time and at regular time intervals. To this end, the flow of $CaO_2$ powder was adjusted to 3 g/min.

After the addition of whole the $CaO_2$ powder the spraying of the remainder of the polycaprolactone solution was continued. After this, the drum was still rotated for another 2 min. The operation took 15 min on the whole.

The so-coated seeds were then removed from the drum and spread out in a 2 cm thin layer on a china plate at ambiant temperature and under an efficient ventilation so as to achieve a quick and complete evaporation of the $CH_2Cl_2$ still present in the coating. After 30 min in these conditions, all the solvent odour disappeared and the seeds were ready to use.

The coated seeds were then left to germinate on moist filter paper (example 2). The germination tests were carried out at 20° to 22° C.

A germination test with uncoated seeds was carried out by way of comparison (example 1R).

The characteristics of the coating agent and the results obtained are summarised in table 1.

TABLE 1

| EXAMPLES | 1R | 2 |
| --- | --- | --- |
| Coating agent | | |
| g/100 g seeds CAPA 520* | — | 5 |
| Commercial $CaO_2$ (60% of $CaO_2$) | — | 10 |
| Rate of germination % | | |
| after 3 to 4 days | 96 | 100 |
| Strength of the seedling. | | |
| g/seedling weight of the seedlings after 3–4 days | 1.375 | 1.550 |

*polycaprolactone marketed by INTEROX.

No phytotoxic effect was observed on the cotyledons as a result of calcium peroxide, unlike the coatings containing no polycaprolactone.

EXAMPLES 3R AND 4

COATING AND GERMINATION OF PEA SEEDS 200 g of Oberon pea seeds were coated (example 4) with a 50% by weight solution of polycaprolactone in methylene chloride in the same coating device and according to the same coating technique as in example 2.

The coated seeds were then left to germinate on moist filter paper. The germination tests were carried out at 20°–22° C.

A germination test with uncoated seeds was carried out by way of comparison (example 3R).

The characteristics of the coating agent and the results obtained are summarised in table 2.

TABLE 2

| EXAMPLES | 3R | 4 |
| --- | --- | --- |
| Coating agent | | |
| g/100 g seeds CAPA 215* | — | 4.5 |
| Commercial $CaO_2$ (60% of $CaO_2$) | — | 10 |
| Rate of germination % | | |
| after 4–5 days | 87 | 100 |
| Strength of the seedling. | | |
| g/seedling weight of the seedlings after 4–5 days | 0.401 | 0.506 |

*polycaprolactone marketed by INTEROX.

No phytotoxic effect on the cotyledons as a result of calcium peroxide was observed, unlike the coatings containing no polycaprolactone.

EXAMPLE 5

COATING OF PEA SEEDS

In a circular drum like the one used in the previous examples, 200 g of Oberon pea seeds were added. The drum was then rotated at 50 rotations/min and the seeds and the plate were then heated at approximately 40° C. with an hot air flow supplied by a ventilator fitted with a 1 500 watts resistor.

The amount (3 g) of poly-ε-caprolactone was then melted at 50° C. and poured in a pneumatic spraying appliance like the one from the previous examples and with a tank maintained at 70° C. by an electric heating mantel wounded onto its external surface.

The seeds were coated by a first and regular layer of 0.3 g of polycaprolactone then the addition of a commercial calcium peroxyde powder of 60 weight % of $CaO_2$ was started by the same vibrating doser than in the previous examples. The addition of powder was done with a flow of 2 g/min at the same time with the spraying at regular time intervals of the polycaprolactone so as to give a regular coating of the seeds.

The operation in its whole took 20 min and required the use of 3 g of molten polycaprolactone. After the coating, the coated seeds were removed from the drum and spread in a 5 cm thin layer on a china plate at ambiant temperature. After cooling, the seeds were ready for use.

We claim:

1. A process for preparing coated seeds, comprising applying, in the absence of water, a peroxy compound and a solution of a polyester in an organic solvent to uncoated seeds, and removing the organic solvent to produce dry, coated seeds.

2. The process of claim 1, wherein the peroxide compound and polyester solution are applied simultaneously.

3. The process of claim 1, wherein the peroxide compound and polyester solution are applied in successive steps.

4. A process for preparing coated seeds according to claim 1, comprising applying, in the absence of water, a peroxy compound and a liquid phase polyester to uncoated seeds.

5. The process of claim 4, wherein the peroxide compound and liquid phase polyester are applied simultaneously.

6. The process of claim 4, wherein the peroxide compound and liquid phase polyester are applied in successive steps.

7. Seeds coated with an anhydrous coating composition consisting essentially of a peroxy compound and a poly(caprolactone) having a melting point of 80° C. or less.

8. Coated seeds according to claim 7, wherein the poly(caprolactone) is a polymer of $\epsilon$-polycaprolactone.

9. Coated seeds acording to claim 7 wherein the peroxy compound is an alkaline earth metal peroxide.

10. Coated seeds according to claim 9, wherein the peroxy compound is calcium peroxide.

11. Coated seeds according to claim 7, wherein the coating composition is present in amounts of from 0.01 to 200% of the weight of the uncoated seeds, said coating agent comprising from 5 to 60% by weight poly(caprolactone) and from 40 to 95% by weight peroxy compounds.

12. Coated seeds according to claim 7, wherein the anhydrous coating composition consists essentially of one or more poly(caprolactones) and one or more peroxide compound.

13. Coated seeds according to claim 7, wherein the anhydrous coating composition consists essentially of one or more poly(caprolactones), one or more peroxide compounds, and at least one additive selected form the group consisting of insecticides, nematicides, fungicides, disinfectants, repallants, herbicides, growth regulators, selective herbicide inhibitors, nutrients, germination aids, and beneficial bacteria.

14. Seeds coated with an anhydrous coating composition consisting essentially of a peroxy compound, and a poly(caprolactone) having a melting point of 80° C. or less, and at least one additive chosen from the group consisting of fillers, plant health products and nutrients.

15. Coated seeds according to claim 14, wherein the coating composition is present in amounts of from 0.01 to 300% of the weight of the uncoated seeds, said coating agent consisting essentially of from 0.1 to 50% by weight poly(caprolactone), from 30 to 75% by weight peroxy compounds and from 20 to 60% by weight various additives.

16. Coated seeds according to claim 14, wherein the coating composition is present in amounts of 0.5 to 100 times the weight of the uncoated seeds, said coating agent consisting essentially of from 0.1 to 20% by weight poly(caprolactone), from 0.1 to 30% by weight peroxy compounds, from 30 to 99.7% by weight fillers and from 0.01 to 30% by weight other additives.

* * * * *

UNITED STATES PATENT AND TRADEMARK OFFICE
CERTIFICATE OF CORRECTION

PATENT NO. : 5,044,116
DATED : September 3, 1991
INVENTOR(S) : Ignace Gago et al.

It is certified that error appears in the above-identified patent and that said Letters Patent is hereby corrected as shown below:

On the title page, item [30]: change the
Foreign Application Priority Data, to read as follows:

December 12, 1983   [FR]   France   ......... 83 19981

Signed and Sealed this

Twentieth Day of October, 1992

*Attest:*

DOUGLAS B. COMER

*Attesting Officer*     *Acting Commissioner of Patents and Trademarks*